(12) United States Patent
Hoffman

(10) Patent No.: US 8,481,498 B1
(45) Date of Patent: Jul. 9, 2013

(54) PHARMACEUTICAL COMPOSITIONS AND METHODS

(76) Inventor: Steven Hoffman, Mahwah, NJ (US)

(*) Notice: Subject to any disclaimer, the term of this patent is extended or adjusted under 35 U.S.C. 154(b) by 0 days.

(21) Appl. No.: 13/371,076

(22) Filed: Feb. 10, 2012

Related U.S. Application Data

(60) Provisional application No. 61/587,420, filed on Jan. 17, 2012.

(51) Int. Cl.
*A61K 38/00* (2006.01)
*A61P 35/00* (2006.01)

(52) U.S. Cl.
USPC ........ 514/19.3; 514/19.4; 514/19.8; 514/19.2

(58) Field of Classification Search
USPC .............................. 514/19.2, 19.3, 19.4, 19.8
See application file for complete search history.

(56) References Cited

U.S. PATENT DOCUMENTS

| | | | |
|---|---|---|---|
| 4,117,161 | A | 9/1978 | Pozuelo |
| 4,165,382 | A | 8/1979 | Pozuelo |
| 4,189,604 | A | 2/1980 | Umezawa et al. |
| 4,240,975 | A | 12/1980 | Umezawa et al. |
| 5,073,541 | A | 12/1991 | Taylor et al. |
| 5,206,018 | A | 4/1993 | Sehgal et al. |
| 5,576,290 | A | 11/1996 | Hadley |
| 5,674,839 | A | 10/1997 | Hruby et al. |
| 5,683,981 | A | 11/1997 | Hadley et al. |
| 5,714,576 | A | 2/1998 | Hruby et al. |
| 6,359,001 | B1 | 3/2002 | Drago |
| 7,452,868 | B2 | 11/2008 | Kuzma et al. |
| 2002/0128304 | A1 | 9/2002 | D'Amato |
| 2003/0059471 | A1* | 3/2003 | Compton et al. ............ 424/489 |
| 2006/0063699 | A1 | 3/2006 | Larsen |
| 2009/0030067 | A1 | 1/2009 | Wosikowski-Buters |
| 2010/0216781 | A1 | 8/2010 | Perrin-Ninkovic |

FOREIGN PATENT DOCUMENTS

| | | |
|---|---|---|
| WO | WO 02/100885 | 12/2002 |
| WO | WO 2009/054001 | 4/2009 |
| WO | WO 2009/109649 | 9/2009 |
| WO | WO 2009/131631 | 10/2009 |
| WO | WO 2010/022243 | 2/2010 |
| WO | WO 2010/118419 | 10/2010 |
| WO | WO 2011/112576 | 9/2011 |

OTHER PUBLICATIONS

Chiu, G.N.C., et al., "Lipid-Based Nanoparticulate Systems for the Delivery of Anti-Cancer Drug Cocktails: Implications on Pharmacokinetics and Drug Toxicities," Current Drug Metabolism 10:861-874 (2009).*

Brogden, R.N., et al., "α-Methyl-p-Tyrosine: A review of its Pharmacology and Clinical Use," Drugs 21:81-89 (1981).*
Ryakhovsky, V.V., et al., "The first preparative solution phase synthesis of melanotan II," Beilstein Journal of Organic Chemistry 4:1-6 (2008).*
Landmark, C.J., "Antiepileptic Drugs in Non-Epilepsy Disorders—Relations between Mechanisms of Action and Clinical Efficacy," CNS Drugs 22:27-47 (2008).*
Terauchi, M., et al., "Inhibition of APN/CD13 leads to suppressed progressive potential in ovarian carcinoma cells," BMC Cancer 7:1-12 (2007).*
Böni et al., "Radioiodine-labelled alpha-methyl-tyrosine in malignant melanoma: cell culture studies and results in patients", British Journal of Dermatology, Jul. 1997, vol. 137, Issue 1, 96-100.
Brogden, "alpha-Methyl-p-tyrosine: a review of its pharmacology and clinical use", Drugs, Feb. 1981, 21(2), 81-89.
Cabrera López et al., "Effects of rapamycin on angiomyolipomas in patients with tuberous sclerosis", Nefrologia, Apr. 2011, 31(3), 292-298.
Chen, "Progress in the development of bestatin analogues as aminopeptidases inhibitors", Current Medical Chemistry, Mar. 2011, vol. 18, No. 7, 964-976.
Chhun et al., "7. The Cytochrome P-450 2C9/2C19 but Not the ABCB1 Genetic Polymorphism May Be Associated With the Liver Cytochrome 3A4 Induction by Phenytoin", Journal of Clinical Psychopharmacology, Jun. 2012, vol. 32, No. 3, 429-431.
Dorr et al., "Evaluation of melanotan-II, a superpotent cyclic melanotropic peptide in a pilot phase-I clinical study", Life Sciences, Apr. 1996, vol. 58, Issue 20, 1777-1784.
Ell, "Brain tumor uptake of iodo-alpha-methyl-tyrosine", Journal of Nuclear Medicine, Nov. 1991, 32(11), 2193-2194.
Espeillac et al., "S6 kinase 1 is required for rapamycin-sensitive liver proliferation after mouse hepatectomy", The Journal of Clinical Investigation, Jul. 2011, 121(7), 2821-2832.
Fan et al., "Impact of system L amino acid transporter 1 (LAT1) on proliferation of human ovarian cancer cells: a possible target for combination therapy with anti-proliferative aminopeptidase inhibitors", Biochemical Pharmacology, Sep. 15, 2010, vol. 80, Issue 6, 811-818.

(Continued)

*Primary Examiner* — Christina Bradley
*Assistant Examiner* — Kristina M Hellman
(74) *Attorney, Agent, or Firm* — Woodcock Washburn LLP

(57) ABSTRACT

Pharmaceutical compositions and kits including a tyrosine hydroxylase inhibitor, a melanin promoter, a p450 3A4 promoter, and a leucine aminopeptidase inhibitor are provided. Also provided are methods of treating cancer in a subject, comprising administering an effective amount of a tyrosine hydroxylase inhibitor, a melanin promoter, a p450 3A4 promoter, and a leucine aminopeptidase inhibitor to the subject in need thereof. Also provided are methods of reducing cell proliferation in a subject comprising administering an effective amount of a tyrosine hydroxylase inhibitor, a melanin promoter, a p450 3A4 promoter, and a leucine aminopeptidase inhibitor to the subject in need thereof.

30 Claims, No Drawings

OTHER PUBLICATIONS

Fitzgerald et al., "Effect of Melanotan, [Nle(4), D-Phe(7)]-alpha-MSH, on melanin synthesis in humans with MC1R variant alleles", Peptides, Feb. 2006, vol. 27, Issue 2, 388-394.

Ichimura et al., "Immunohistochemical expression of aminopeptidase N (CD13) in human lung squamous cell carcinomas, with special reference to Bestatin adjuvant therapy", Pathology International, Jun. 2006, vol. 56, Issue 6, 296-300.

Kargiotis et al., "Epilepsy in the cancer patient", Cancer Chemotherapy and Pharmacology, Mar. 2011, vol. 67, No. 3, 489-501.

Krige et al., "CHR-2797: An antiproliferative aminopeptidase inhibitor that leads to amino acid deprivation in human leukemic cells", Cancer Research, Aug. 15, 2008, 68(16), 6669-6679.

Kulke et al., "Future directions in the treatment of neuroendocrine tumors: consensus report of the National Cancer Institute Neuroendocrine Tumor clinical trials planning meeting", Journal of Clinical Oncology, Mar. 2011, vol. 29, No. 7, 934-943.

Liu et al., "Combinatorial effects of lapatinib and rapamycin in triple-negative breast cancer cells", Molecular Cancer Therapeutics, Aug. 2011, 10, 1460-1469.

Longo et al., "Efficacy and tolerability of long-acting octreotide in the treatment of thymic tumors: results of a pilot trial", American Journal of Clinical Oncology, Apr. 2012, 35(2), 105-109.

Nakagami, "A case of malignant pheochromocytoma treated with 131I-metaiodobenzylguanidine and alpha-methyl-p-tyrosine", Japanese Journal of Medicine, May-Jun. 1990, vol. 29, No. 3, 329-333.

Ram et al., "Failure of alpha-methyltyrosine to prevent hypertensive crisis in pheochromocytoma", Archives of Internal Medicine, Nov. 1985, vol. 145, No. 11, 2114-2115.

Steinsapir et al., "Metyrosine and pheochromocytoma", Archives of Internal Medicine, Apr. 1997, vol. 157, No. 8, 901-906.

Tada, "Three cases of malignant pheochromocytoma treated with cyclophosphamide, vincristine, and dacarbazine combination chemotherapy and alpha-methyl-p-tyrosine to control hypercatecholaminemia", Hormone Research, Jan. 1998, vol. 49, No. 6, 295-297.

Taveria-DaSilva, "Sirolimus therapy in patients with lymphangioleiomyomatosis", Summaries for patients, Annals of Internal Medicine, Jun. 21, 2011, 154(12), I44.

Tsukamoto et al., "Aminopeptidase N (APN)/CD13 inhibitor, Ubenimex, enhances radiation sensitivity in human cervical cancer", BMC Cancer, Mar. 2008, 8:74, 8 pages.

Voorhess, "Effect of alpha-methyl-p-tyrosine on 3,4-dihydroxyphenylalanine (DOPA) excretion of hamsters with melanotic melanoma", Cancer Research, Mar. 1968, 28, 452-454.

Zimmermann et al., "Prolonged Inhibition of Presynaptic Catecholamine Synthesis With $\alpha$-Methyl-Para-Tyrosine Attenuates the Circadian Rhythm of Human TSH Secretion" J. Soc. Gynecol Investing, May/Jun. 2001, vol. 8 No. 3, 174-178.

\* cited by examiner

PHARMACEUTICAL COMPOSITIONS AND METHODS

CROSS-REFERENCE TO RELATED APPLICATION

This application claims the benefit of U.S. Provisional Application No. 61/587,420, filed Jan. 17, 2012, which is incorporated herein by reference in its entirety.

TECHNICAL FIELD

The present inventions relate generally to compositions, kits and methods for the reduction of cellular proliferation as, for example, in the treatment of cancer.

BACKGROUND

According to the U.S. National Cancer Institute's Surveillance Epidemiology and End Results (SEER) database for the year 2008, the most recent year for which incidence data are available, 11,958,000 Americans have invasive cancers. Cancer is the second most common cause of death in the United States, behind only heart disease, and accounts for one in four deaths. It has been estimated that approximately 1600 Americans die of cancer each day. In addition to the medical, emotional and psychological costs of cancer, cancer has significant financial costs to both the individual and society. It is estimated by the National Institutes of Health that the overall costs of cancer in 2010 was $263.8 billion. In addition, it is estimated that another $140.1 billion is lost in productivity due to premature death.

Cancer treatments today include surgery, hormone therapy, radiation, chemotherapy, immunotherapy, targeted therapy, and combinations thereof. Surgical removal of cancer has advanced significantly; however, there remains a high chance of recurrence of the disease. Hormone therapy using drugs such as aromatase inhibitors and luteinizing hormone-releasing hormone analogs and inhibitors has been relatively effective in treating prostate and breast cancers. Radiation and the related techniques of conformal proton beam radiation therapy, stereotactic radiosurgery, stereotactic radiation therapy, intraoperative radiation therapy, chemical modifiers, and radio sensitizers are effective at selectively killing cancerous cells, but can also kill and alter surrounding normal tissue. Chemotherapy drugs such as aminopterin, cisplatin, methotrexate, doxorubicin, daunorubicin and others alone and in combinations are effective at selectively killing cancer cells, often by altering the DNA replication process. Biological response modifier (BRM) therapy, biologic therapy, biotherapy, or immunotherapy alter cancer cell growth or influence the natural immune response, and involve administering biologic agents to a patient such as an interferons, interleukins, and other cytokines and antibodies such as rituximab and trastuzumab and even cancer vaccines such as Sipuleucel-T.

Recently, new targeted therapies have been developed to fight cancer. These targeted therapies differ from chemotherapy because chemotherapy works by killing both cancerous and normal cells, with greater effects on the cancerous cells. Targeted therapies work by influencing the processes that control growth, division, and the spread of cancer cells and signals that cause cancer cells to die naturally. One type of targeted therapy includes growth signal inhibitors such as trastuzumab, gefitinib, imatinib, centuximab, dasatinib and nilotinib. Another type of targeted therapy includes angiogenesis inhibitors such as bevacizumab that inhibit cancers from increasing surrounding vasculature and blood supply. A final type of targeted therapy includes apoptosis-inducing drugs that are able to induce direct cancer cell death.

Although all of these treatments have been effective to one degree or another, they all have drawbacks and limitations. In addition to many of the treatments being expensive, they also are often too imprecise or the cancers are able to adapt to them and become resistant.

Thus, there is a great need for additional cancer treatments. In particular, there is a need for treatments for cancers that have become resistant to other forms of treatment.

SUMMARY

The present invention provides compositions, kits, and methods for reducing undue cellular proliferation, including that associated with the treatment of cancer. In certain embodiments, the invention provides pharmaceutical compositions comprising at least one tyrosine hydroxylase inhibitor, at least one melanin promoter, at least one p450 3A4 promoter, at least one leucine aminopeptidase inhibitor, and, optionally, at least one growth hormone inhibitor. In other embodiments, the invention provides kits that comprise these components together with suitable packaging. Also provided are methods of reducing cellular proliferation and/or methods of treating cancer comprising administering an effective amount of at least one tyrosine hydroxylase inhibitor, at least one melanin promoter, at least one p450 3A4 promoter, at least one leucine aminopeptidase inhibitor, and, optionally, at least one growth hormone inhibitor to the subject in need thereof.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) includes preventative (e.g., prophylactic), curative or palliative treatment. As used herein, the term "treating" includes alleviating or reducing at least one adverse or negative effect or symptom of a condition, disease or disorder. This condition, disease or disorder can be cancer.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

In one embodiment, the present invention provides combination therapies that alter the defenses of cancerous cells to oxidative stress. One class of such therapies increases free radical availability to cancerous cells. A representative subclass of such therapies involve administration of pharmaceutical compositions comprising a tyrosine hydroxylase inhibitor, a melanin promoter, a p450 3A4 promoter, a leucine aminopeptidase inhibitor, and, optionally, a growth hormone inhibitor. Particular components of the pharmaceutical composition are described below.

While not intending to be bound by any particular mechanism of operation, tyrosine hydroxylase inhibitors according to the present invention function by accumulating in cancer cells and preventing them from forming a coating of either lipids or hyaluronan. By preventing the cancer cells from forming a coating of either lipids or hyaluron, the cancer cells are believed to be made more accessible to oxidative stress. Representative tyrosine hydroxylase inhibitors include tyrosine derivatives, which typically are rapidly absorbed by most cancers and inflamed tissues. Representative tyrosine derivatives include one or more of methyl (2R)-2-amino-3-(2-chloro-4-hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl) propanoate, methyl (2R)-2-amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl)propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride, methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-$I_2$)—OSu, Fmoc-tyr(3-$NO_2$)—OH, and α-methyl-DL-tyrosine.

Melanin promoters according to the present invention are chemical compounds that increase the production and/or the activity of melanin. Increased melanin levels are believed to reduce inflammation (through, for example, suppression of TNF) and exclude the sequestered lymph system. Melanin also is a photo catalyst, and can therefore promote chemical reactions which generate free radicals which, in turn, can become accessible to cancer cells. Representative melanin promoters are methoxsalen and melanotan II.

The pharmaceutical compositions of the invention also include a p450 3A4 promoter. "Cytochrome p450 3A4" (which can be abbreviated as "p450 3A4") is a member of the cytochrome p450 superfamily of enzymes, and is a mixed-function oxidase that is involved in the metabolism of xenobiotics in the body. It has the widest range of substrates of all of the cytochromes. The function of a p450 3A4 promoter in the pharmaceutical compositions of the invention is to increase the expression and/or the activity of p450 3A4. The increased p450 3A4 expression and/or activity is believed to reduce cortisone and estrogen levels in the patient. Additionally, the increased p450 3A4 expression and/or activity also slightly increases blood pH, which is believed to help to preserve or enhance melanin activity. Representative p450 3A4 promoters are 5,5-diphenylhydantoin, valproic acid, and carbamazepine, which are believed to induce expression of the p450 3A4 enzyme.

The instant pharmaceutical compositions further include leucine aminopeptidase inhibitors (alternatively known as leucyl aminopeptidase inhibitors). Leucine aminopeptidases are enzymes that preferentially catalyze the hydrolysis of leucine residues at the N-terminus of peptides and/or proteins. Inhibiting the expression and/or activity of leucine aminopeptidases is believed to assist in tumor reabsorption by increasing cholesterol transport to the liver. Generally, it is believed that aminopeptidase inhibitors, including aminopeptidase inhibitors, deplete sensitive tumor cells of specific amino acids by preventing protein recycling, thus generating an antiproliferative effect. Representative leucine aminopeptidase inhibitors are N-[(2S,3R)-3-amino-2-hydroxy-4-phenylbutyryl]-L-leucine, and rapamycin.

The suitable instant pharmaceutical compositions also optionally includes a growth hormone inhibitor. Growth hormone (such as, for example, pancreatic growth hormone) induces cell replication. Inhibition of the expression and/or activity of growth hormone is believed to exclude normal cells from rapid replication while allowing cancer cells to continue to rapidly replicate and incorporate the tyrosine derivative. Representative growth hormone inhibitors are octreotide, somatostatin, and seglitide.

The pharmaceutical compositions of the invention can further include D-leucine. D-leucine is a stereoisomer of the naturally occurring L-leucine, the form of leucine incorporated into polypeptides and proteins. D-leucine cannot be incorporated into polypeptides and/or proteins. Along with the leucine aminopeptidase inhibitor, the D-leucine is believed to create a physiological environment that mimics a leucine shortage. Thus, the presence of D-leucine permits the use of lower doses of leucine aminopeptidase inhibitor in a pharmaceutical composition.

Also provided herein are kits including a combination therapy that creates alterations in the defenses of cancerous cells to oxidative stress. An intended suitable embodiment is a kit that includes a combination therapy that increases free radical availability to cancerous cells. Representative kits comprise a tyrosine hydroxylase inhibitor, a melanin promoter, a p450 3A4 promoter, a leucine aminopeptidase inhibitor and, optionally, a growth hormone inhibitor of the type described above, together with packaging for same. The kit can include one or more separate containers, dividers or compartments and, optionally, informational material such as instructions for administration. For example, each inhibitor or promoter (or the various combinations thereof) can be contained in a bottle, vial, or syringe, and the informational material can be contained in a plastic sleeve or packet or provided in a label. In some embodiments, the kit includes a plurality (e.g., a pack) of individual containers, each containing one or more unit dosage forms of a compound described herein. For example, the kit can include a plurality of syringes, ampules, foil packets, or blister packs, each containing a single unit dose of a compound described herein or any of the various combinations thereof. The containers of the kits can be air tight, waterproof (e.g., impermeable to changes in moisture or evaporation), and/or light-tight. The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

Methods of treating cancer in a subject also are provided, as are methods of reducing undue cellular proliferation. Such methods can include administering an effective amount of a combination therapy that creates alterations in the defenses of cancerous cells to oxidative stress. Representative methods of treating cancer include administering an effective amount of a combination therapy that increases free radical availability to cancerous cells. Suitable embodiments are methods that include administering an effective amount of the above-noted tyrosine hydroxylase inhibitor, melanin promoter, p450 3A4 promoter, leucine aminopeptidase inhibitor and, optionally, growth hormone inhibitor.

Suitable methods include simultaneous or at least contemporaneous administration of at least two of the tyrosine hydroxylase inhibitor, melanin promoter, p450 3A4 promoter, and leucine aminopeptidase inhibitor, at least three of them, or each of them (in each case, optionally, with a growth hormone inhibitor). It is believed to be desirable that an effective concentration of these moieties be in the subject's bloodstream at the same time, and any dosing regimen that achieves this is within the scope of the present invention. The desired number of inhibitors and promoters can be provided in a single dosage form or any number of desired dosage forms, including in individual dosage forms. Representative dosage forms include tablets, capsules, caplets, sterile aqueous or organic solutions, and colloidal suspensions. The amount of composition administered will, of course, be dependent on the subject being treated, the subject's weight, the severity of the condition being treated, the manner of administration, and the judgment of the prescribing physician.

Administration of the promoters and inhibitors can be through various routes, including orally, subcutaneously, intravenously, transdermally, vaginally, rectally or in any combination thereof. Transdermal administration can be effected using, for example, oleic acid, 1-methyl-2-pyrrolidone, or dodecylnonaoxyethylene glycol monoether.

The promoters and inhibitors can be administered during a cycle consisting of five to seven days of administering the promoters and inhibitors and one to two days of not administering the promoters and inhibitors. The promoters and inhibitors can be administered over the course of at least six of said cycles.

The subject to which the instant compositions are administered can be a mammal, preferably a human.

In one representative method, 60 mg of the tyrosine derivative is administered orally and 0.25 mL of a 2 mg/mL suspension of the tyrosine derivative is administered subcutaneously; 10 mg of the methoxsalen is administered orally and 0.25 mL of a 1 mg/mL suspension of the methoxsalen is administered subcutaneously; 30 mg of the 5,5-diphenylhydantoin is administered orally; and 20 mg of the N-[(2S,3R)-3-amino-2-hydroxy-4-phenylbutyryl]-L-leucine is administered orally.

Representative methods include those in which the cancer is non-small cell lung cancer. In certain embodiments, the non-small cell lung cancer is stage IV non-small cell lung cancer. In yet other embodiments, the cancer is ovarian cancer, breast cancer, cervical cancer, pancreatic cancer, stomach cancer, brain cancer, liver cancer, or testicular cancer. The cancer can also be leukemia or lymphoma.

In certain embodiments, one or more of the tyrosine hydroxylase inhibitor; the melanin promoter; the p450 3A4 promoter; and the leucine aminopeptidase inhibitor is a nucleic acid, protein, antibody or antigen-binding fragment of an antibody.

The present methods can include not only the disclosed administration step but also the step of assessing progression of said cancer in said subject and/or the extent of cellular proliferation. The assessing step can be performed before or after the administering step.

Suitable embodiments can include a pharmaceutical composition comprising a tyrosine hydroxylase inhibitor, a melanin promoter, a p450 3A4 promoter, and a leucine aminopeptidase inhibitor. The pharmaceutical composition can further comprise a growth hormone inhibitor. The growth hormone can be pancreatic growth hormone. The growth hormone inhibitor can be octreotide or somatostatin. The tyrosine hydroxylase inhibitor can be a tyrosine derivative. The tyrosine derivative can be one or more of methyl (2R)-2-amino-3-(2-chloro-4 hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl)propanoate, methyl (2R)-2-amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl)propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride, methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. The melanin promoter can be methoxsalen or melanotan II. The p450 3A4 promoter can be 5,5-diphenylhydantoin. The p450 3A4 promoter can be valproic acid or carbamazepine. The leucine aminopeptidase inhibitor can be N-[(2S,3R)-3-amino-2-hydroxy-4-phenylbutyryl]-L-leucine or rapamycin. The pharmaceutical compositions of the invention can further comprise D-leucine.

Also provided herein are kits comprising a tyrosine hydroxylase inhibitor, a melanin promoter, a p450 3A4 promoter, and a leucine aminopeptidase inhibitor, together with packaging for same. The kit can further comprise a growth hormone inhibitor. The growth hormone can be pancreatic growth hormone. The growth hormone inhibitor can be octreotide or somatostatin. The tyrosine hydroxylase inhibitor can be a tyrosine derivative. The tyrosine derivative can be one or more of methyl (2R)-2-amino-3-(2-chloro-4 hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl)propanoate, methyl (2R)-2-amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-$I_2$)—OSu, Fmoc-tyr(3-$NO_2$)—OH, and α-methyl-DL-tyrosine. The melanin promoter can be methoxsalen or melanotan II. The p450 3A4 promoter can be 5,5-diphenylhydantoin, valproic acid or carbamazepine. The leucine aminopeptidase inhibitor can be N-[(2S,3R)-3-amino-2-hydroxy-4-phenylbutyryl]-L-leucine or rapamycin. The kits of the invention can further comprise D-leucine.

Methods of treating cancer in a subject are also provided comprising administering an effective amount of a tyrosine hydroxylase inhibitor, a melanin promoter, a p450 3A4 promoter, and a leucine aminopeptidase inhibitor to the subject in need thereof. In a suitable embodiment, the method of treating cancer can further comprise a growth hormone inhibitor. In certain embodiments, at least two of the promoters and inhibitors are administered simultaneously. In other embodiments, at least three of the promoters and inhibitors are administered simultaneously. Each of the promoters and inhibitors can be administered simultaneously. In suitable embodiments, the promoters and inhibitors are administered orally, subcutaneously, intravenously, transdermally, vaginally, rectally or in any combination thereof. The transdermal administration can be done with oleic acid, 1-methyl-2-pyrrolidone, or dodecylnonaoxyethylene glycol monoether. In other embodiments, the promoters and inhibitors are administered during a cycle consisting of five to seven days of administering the promoters and inhibitors and one to two days of not administering the promoters and inhibitors. The promoters and inhibitors can be administered over the course of at least six of said cycles. The tyrosine hydroxylase inhibitor can be a tyrosine derivative. The tyrosine derivative can be one or more of methyl (2R)-2-amino-3-(2-chloro-4 hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl)propanoate, methyl (2R)-2-amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride, methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-$I_2$)—OSu, Fmoc-tyr(3-$NO_2$)—OH, and α-methyl-DL-tyrosine. In a suitable embodiment of the method, 60 mg of the tyrosine derivative is administered orally and 0.25 mL of a 2 mg/mL suspension of the tyrosine derivative is administered subcutaneously. The melanin promoter can be methoxsalen. In another suitable method, 10 mg of the methoxsalen is administered orally and 0.25 mL of a 1 mg/mL suspension of the methoxsalen is administered subcutaneously. The melanin promoter can also be melanotan II. The p450 3A4 promoter can be 5,5-diphenylhydantoin. In another suitable method, 30 mg of the 5,5-diphenylhydantoin is administered orally. The p450 3A4 promoter can also be valproic acid or carbamazepine. The leucine aminopeptidase inhibitor can be N-[(2S,3R)-3-amino-2-hydroxy-4-phenylbutyryl]-L-leucine. In another suitable method, 20 mg of the N-[(2S,3R)-3-amino-2-hydroxy-4-phenylbutyryl]-L-leucine is administered orally. The leucine aminopeptidase inhibitor can also be rapamycin. The growth hormone can be pancreatic growth hormone. The growth hormone inhibitor can be octreotide. The method can further comprise administering an effective amount of D-leucine. The subject can be a mammal and that mammal can be a human. Representative methods include those in which the cancer is non-small cell lung cancer. In certain embodiments, the non-small cell lung cancer is stage IV non-small cell lung cancer. In other embodiments, the cancer is ovarian cancer, breast cancer, cervical cancer, pancreatic cancer, stomach cancer, brain cancer, liver cancer, or testicular cancer. In other embodiments, the cancer is leukemia or lymphoma. In other suitable embodiments, the tyrosine hydroxylase inhibitor, the melanin promoter, the p450 3A4 promoter, and the leucine aminopeptidase inhibitor is one or more of a nucleic acid, protein, antibody or antigen-binding fragment of an antibody. Another suitable embodiment further comprises assessing progression of said cancer in said subject. The assessing step can be performed before said administering step or the assessing step can be performed after said administering step.

Methods of reducing cell proliferation in a subject are also provided comprising administering an effective amount of a tyrosine hydroxylase inhibitor; a melanin promoter; a p450 3A4 promoter; and a leucine aminopeptidase inhibitor to the subject in need thereof. In a suitable embodiment, the method of treating cancer can further comprise a growth hormone inhibitor. In certain embodiments, at least two of the promoters and inhibitors are administered simultaneously. In other embodiments, at least three of the promoters and inhibitors are administered simultaneously. Each of the promoters and inhibitors can be administered simultaneously. In suitable embodiments, promoters and inhibitors are administered orally, subcutaneously, intravenously, transdermally, vaginally, rectally or in any combination thereof. The transdermal administration can be done with oleic acid, 1-methyl-2-pyrrolidone, or dodecylnonaoxyethylene glycol monoether. In other embodiments, the promoters and inhibitors are administered during a cycle consisting of five to seven days of administering the promoters and inhibitors and one to two days of not administering the promoters and inhibitors. The promoters and inhibitors can be administered over the course of at least six of said cycles. The tyrosine hydroxylase inhibitor can be a tyrosine derivative. The tyrosine derivative can be one or more of methyl (2R)-2-amino-3-(2-chloro-4 hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl)propanoate, methyl (2R)-2- amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride, methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. In a suitable embodiment of the method, 60 mg of the tyrosine derivative is administered orally and 0.25 mL of a 2 mg/mL suspension of the tyrosine derivative is administered subcutaneously. The melanin promoter can be methoxsalen. In another suitable method, 10 mg of the methoxsalen is administered orally and 0.25 mL of a 1 mg/mL suspension of the methoxsalen is administered subcutaneously. The melanin promoter can also be melanotan II. The p450 3A4 promoter can be 5,5-diphenylhydantoin. In another suitable method, 30 mg of the 5,5-diphenylhydantoin is administered orally. The p450 3A4 promoter can also be valproic acid or carbamazepine. The leucine aminopeptidase inhibitor can be N-[(2S,3R)-3-amino-2-hydroxy-4-phenylbutyryl]-L-leucine. In another suitable method, 20 mg of the N-[(2S,3R)-3-amino-2-hydroxy-4-phenylbutyryl]-L-leucine is administered orally. The leucine aminopeptidase inhibitor can also be rapamycin. The growth hormone can be pancreatic growth hormone. The growth hormone inhibitor can be octreotide. The method can further comprise administering an effective amount of D-leucine. The subject can be a mammal and the mammal can be a human. Representative methods include those in which the cancer is non-small cell lung cancer. In certain embodiments, the non-small cell lung cancer is stage IV non-small cell lung cancer. In other embodiments, the cancer is ovarian cancer, breast cancer, cervical cancer, pancreatic cancer, stomach cancer, brain cancer, liver cancer, or testicular cancer. In other embodiments, the cancer is leukemia or lymphoma. In other suitable embodiments, the tyrosine hydroxylase inhibitor, the melanin promoter, the p450 3A4 promoter, and the leucine aminopeptidase inhibitor is one or more of a nucleic acid, protein, antibody or antigen-binding fragment of an antibody. Another suitable embodiment further comprises assessing progression of said cancer in said subject. The assessing step can be performed before said administering step or the assessing step can be performed after said administering step.

What is claimed:

1. A method of treating breast cancer in a subject comprising administering an effective amount of a tyrosine hydroxylase inhibitor; a melanin promoter; a p450 3A4 promoter; and a leucine aminopeptidase inhibitor to the subject in need thereof, wherein:
    the melanin promoter is methoxsalen or melanotan II;
    the p450 3A4 promoter is 5,5-diphenylhydantoin, valproic acid, or carbamazepine; and
    the leucine aminopeptidase inhibitor is N-[(2S,3R)-3-amino-2-hydroxy-4-phenylbutyryl]-L-leucine or rapamycin.

2. The method of claim 1 further comprising administering a growth hormone inhibitor.

3. The method of claim 1 wherein at least two of the promoters and inhibitors are administered simultaneously.

4. The method of claim 1 wherein at least three of the promoters and inhibitors are administered simultaneously.

5. The method of claim 1 wherein each of the promoters and inhibitors is administered simultaneously.

6. The method of claim 1 wherein the promoters and inhibitors are administered orally, subcutaneously, intravenously, transdermally, vaginally, rectally or in any combination thereof.

7. The method of claim 6 wherein the transdermal administration is done with oleic acid, 1-methyl-2-pyrrolidone, or dodecylnonaoxyethylene glycol monoether.

8. The method of claim 1 wherein the promoters and inhibitors are administered during a cycle consisting of five to seven days of administering the promoters and inhibitors and one to two days of not administering the promoters and inhibitors.

9. The method of claim 8 wherein the promoters and inhibitors are administered over the course of at least six of said cycles.

10. The method of claim 1 wherein the tyrosine hydroxylase inhibitor is a tyrosine derivative.

11. The method of claim 10 wherein the tyrosine derivative is one or more of methyl (2R)-2-amino-3-(2-chloro-4 hydroxyphenyl)propanoate, D-tyrosine ethyl ester hydrochloride, methyl (2R)-2-amino-3-(2,6-dichloro-3,4-dimethoxyphenyl)propanoate H-D-Tyr(TBU)-allyl ester HCl, methyl (2R)-2-amino-3-(3-chloro-4,5-dimethoxyphenyl)propanoate, methyl (2R)-2-amino-3-(2-chloro-3-hydroxy-4-methoxyphenyl)propanoate, methyl (2R)-2-amino-3-(4-[(2-chloro-6-fluorophenyl)methoxy]phenyl) propanoate, methyl (2R)-2-amino-3-(2-chloro-3,4-dimethoxyphenyl)propanoate, methyl (2R)-2-amino-3-(3-chloro-5-fluoro-4-hydroxyphenyl)propanoate, diethyl 2-(acetylamino)-2-(4-[(2-chloro-6-fluorobenzyl)oxy]benzyl malonate, methyl (2R)-2-amino-3-(3-chloro-4-methoxyphenyl)propanoate, methyl (2R)-2-amino-3-(3-chloro-4-hydroxy-5-methoxyphenyl)propanoate, methyl (2R)-2-amino-3-(2,6-dichloro-3-hydroxy-4-methoxyphenyl)propanoate, methyl (2R)-2-amino-3-(3-chloro-4-hydroxyphenyl)propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, HD-tyr-OMe.HCl, D-tyrosine methyl ester HCl, H-D-Tyr-OMe-HCl, (2R)-2-amino-3-(4-hydroxyphenyl)propionic acid, (2R)-2-amino-3-(4-hydroxyphenyl)methyl ester hydrochloride, methyl (2R)-2-amino-3-(4-hydroxyphenyl)propanoate hydrochloride, methyl (2R)-2-azanyl-3-(4-hydroxyphenyl)propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I2)-OSu, Fmoc-tyr(3-NO2)-OH, and α-methyl-DL-tyrosine.

12. The method of claim 11 wherein 60 mg of the tyrosine derivative is administered orally and 0.25 mL of a 2 mg/mL suspension of the tyrosine derivative is administered subcutaneously.

13. The method of claim 1 wherein the melanin promoter is methoxsalen.

14. The method of claim 13 wherein 10 mg of the methoxsalen is administered orally and 0.25 mL of a 1 mg/mL suspension of the methoxsalen is administered subcutaneously.

15. The method of claim 1 wherein the melanin promoter is melanotan II.

16. The method of claim 1 wherein the p450 3A4 promoter is 5,5-diphenylhydantoin.

17. The method of claim 16 wherein 30 mg of the 5,5-diphenylhydantoin is administered orally.

18. The method of claim 1 wherein the p450 3A4 promoter is valproic acid or carbamazepine.

19. The method of claim 1 wherein the leucine aminopeptidase inhibitor is N-[(2S,3R)-3-amino-2-hydroxy-4-phenylbutyryl]-L-leucine.

20. The method of claim 19 wherein 20 mg of the N-[(2S,3R)-3-amino-2-hydroxy-4-phenylbutyryl]-L-leucine is administered orally.

21. The method of claim 1 wherein the leucine aminopeptidase inhibitor is rapamycin.

22. The method of claim 19 wherein the p450 3A4 promoter is 5,5-diphenylhydantoin.

23. The method of claim 22 wherein the melanin promoter is melanotan II.

24. The method of claim 1 further comprising administering an effective amount of D-leucine.

25. The method of claim 23 wherein the tyrosine derivative is $\alpha$-methyl-DL tyrosine.

26. The method of claim 1 wherein the melanin promoter is melanotan II; the p450 3A4 promoter is 5,5-diphenylhydantoin; and the tyrosine hydroxylase inhibitor is $\alpha$-methyl-DL tyrosine.

27. The method of claim 26 wherein the leucine aminopeptidase inhibitor is N-[(2S,3R)-3-amino-2-hydroxy-4-phenylbutyryl]-L-leucine.

28. The method of claim 26 wherein the leucine aminopeptidase inhibitor is rapamycin.

29. The method of claim 1 further comprising assessing progression of said cancer in said subject.

30. The method of claim 2 further comprising assessing progression of said cancer in said subject.

* * * * *